US 6,706,527 B2

(12) United States Patent
Szecsody

(10) Patent No.: US 6,706,527 B2
(45) Date of Patent: Mar. 16, 2004

(54) AUTOMATED FLUID ANALYSIS APPARATUS AND TECHNIQUES

(75) Inventor: James E. Szecsody, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 510 days.

(21) Appl. No.: 09/809,506

(22) Filed: Mar. 15, 2001

(65) Prior Publication Data
US 2002/0132351 A1 Sep. 19, 2002

(51) Int. Cl.[7] ............................................. G01N 33/24
(52) U.S. Cl. .................. 436/25; 436/52; 436/53; 436/180; 436/179; 436/120; 436/164; 436/55; 422/105; 422/110; 422/114; 422/115; 422/81; 422/63; 422/103; 73/864; 73/864.81; 73/863
(58) Field of Search .......................... 436/25, 52, 53, 436/180, 179, 120, 164, 55; 422/105, 110, 114, 115, 81, 63, 103; 73/864, 863, 864.81

(56) References Cited

U.S. PATENT DOCUMENTS

| 4,520,108 A | * | 5/1985 | Yoshida et al. | ............... 436/52 |
| 5,928,953 A | * | 7/1999 | Kallback | ..................... 436/52 |
| 6,315,952 B1 | * | 11/2001 | Sklar et al. | ................... 422/63 |
| 6,324,924 B1 | * | 12/2001 | Peterson | ..................... 73/864 |

* cited by examiner

Primary Examiner—Jill Warden
Assistant Examiner—Sam P. Siefke
(74) Attorney, Agent, or Firm—Woodard, Emhardt, Moriarty, McNett & Henry, LLP

(57) ABSTRACT

An automated device that couples a pair of differently sized sample loops with a syringe pump and a source of degassed water. A fluid sample is mounted at an inlet port and delivered to the sample loops. A selected sample from the sample loops is diluted in the syringe pump with the degassed water and fed to a flow through detector for analysis. The sample inlet is also directly connected to the syringe pump to selectively perform analysis without dilution. The device is airtight and used to detect oxygen-sensitive species, such as dithionite in groundwater following a remedial injection to treat soil contamination.

17 Claims, 4 Drawing Sheets

US 6,706,527 B2

AUTOMATED FLUID ANALYSIS APPARATUS AND TECHNIQUES

This invention was made with Government support under Contract Number DE-AC0676RLO1830 awarded by the U.S. Department of Energy. The Government has certain rights in the invention.

FIELD OF THE INVENTION

The invention relates to automated fluid analysis. More particularly, but not exclusively, the invention relates to techniques for obtaining the concentration of a chemical in liquid across a widely varying concentration range, and in particular the level of dithionite in groundwater during a remedial soil treatment procedure.

BACKGROUND OF THE INVENTION

Monitoring the levels of particular soil or groundwater constituents is a matter of great concern, and many techniques exist for measuring these concentrations when they remain within a relatively narrow range. However, there are some applications where the concentration of a particular soil constituent is expected to vary across several orders of magnitude. In these situations, it is more difficult and time consuming to obtain accurate data by conventional methods.

For example, soil contamination is often remediated by applying a second chemical into or around the contaminated site. This second chemical, can have beneficial effects by reacting with and decomposing the soil contaminates and/or by forming a barrier to prevent the further spread of the soil contamination. However, this second chemical is sometimes applied in large quantity to a central well and allowed to diffuse or otherwise migrate through the soil. Accordingly, the level of the applied chemical and/or the reaction byproducts at any point in time will likely vary substantially throughout the site depending upon, for example, the distance from the injection well, the local soil conditions, and reaction rate. Knowledge of these time and spacial dependent chemical levels is plainly important in determining the extent and effectiveness of the remediation operation. While groundwater samples can be relatively easily obtained from a group of monitoring wells throughout the site, conventional analysis techniques limit the speed and reliability at which these groundwater samples can be analyzed. Accordingly, conventional analysis techniques limit the ability to have real time knowledge about the remediation process.

One particular remediation method involves the injection of dithionite into the soil and is more fully described in U.S. Pat. No. 5,783,088 to Amonette, the disclosure of which is incorporated by reference. In addition to the problems of widely varying concentrations, dithionite is known to decompose when exposed to oxygen in air or an aqueous environment. This chemical instability necessitates special handling, such as maintaining the sample in an oxygen free environment, further complicating the task of quickly and reliably obtaining an accurate concentration measurement.

One dithionite analysis system has been developed by the present inventors that makes some progress toward meeting this need in the art, but further developments are needed. The present system provides a measured groundwater sample from a sample loop to a syringe pump assembly. There, the sample is diluted with degassed water and injected into a flow through detector. However, the dilution range of this device is limited in that only a single sample size can be provided to the mixing chamber. If the dilution achieved with that single sample size in inadequate, the sample loop must be removed and replaced or manual dilution must be performed. Each of these alternatives is time consuming and undesirable. Accordingly a need exists for a system that can provide multiple dilutions across a widely varying range for rapid and accurate fluid analysis.

In addition, the present device does not provide fully automated undiluted analysis of the groundwater sample. If a diluted groundwater sample is too dilute to produce a useful absorbance signal, an operator must recognize this inadequacy, switch programs, and directly provide the sample to a separate injection port. This too is a complicated process leading to operator error or the simple failure to obtain the data. Especially where numerous samples from multiple wells must be run, a system that can automatically perform direct analysis of a groundwater sample in addition to diluted analysis is needed.

These and other needs are satisfies by various embodiments of the present invention.

SUMMARY OF THE INVENTION

In one aspect the invention comprises a novel fluid analysis system for performing automated fluid analysis over a widely varying concentration range.

In another aspect the invention provides a novel fluid analysis system for performing automated groundwater analysis during a remediation injection. In one aspect the remedial chemical is dithionite.

In one embodiment there is provided a method for monitoring levels of soil chemicals following a remediation injection, comprising: providing a groundwater sample to an apparatus comprising a sample injection assembly operatively coupled to a controller, the injection assembly adapted to selectively provide one of at least two dissimilar predetermined volumes of a fluid sample to a mixing assembly in response to signals received from the controller, the injection assembly including a multiport injection value and at least two sample loops of dissimilar volume, selecting one of the at least two dissimilar predetermined volumes of the fluid sample, transferring the selected volume of the fluid sample to the mixing assembly in response to a signal from the controller, transferring a predetermined volume of dilution fluid to the mixing assembly, mixing the predetermined volumes of dilution fluid and fluid sample to create a first diluted fluid sample, performing a concentration measurement on the first diluted sample. The method can also include selecting a second one of the at least two dissimilar predetermined volumes of the fluid sample, transferring the second selected volume of the fluid sample to the mixing assembly, transferring a second predetermined volume of dilution fluid to the mixing assembly, mixing the second predetermined volumes of dilution fluid and the second selected volume of fluid sample to create a second diluted fluid sample, performing a concentration measurement on the second diluted sample. The method can also include transferring a third selected predetermined volume of fluid to the mixing assembly and performing a concentration measurement on the third fluid sample.

In another embodiment there is provided a novel method for monitoring levels of soil chemicals following a remediation injection, comprising: providing a groundwater sample to an apparatus comprising a sample injection assembly operatively coupled to a controller, the injection assembly adapted to automatically provide one of at least two dissimilar predetermined volumes of a fluid sample to a mixing assembly in response to signals received from the controller, the injection assembly including a multiport valve in fluid communication with at least one sample loop, the injection assembly further including a sample inlet port able to be placed in fluid communication with the multiport valve and the mixing chamber, selecting one of the at least two dissimilar predetermined volumes of the fluid sample, transferring the selected volume of the fluid sample to the mixing assembly in response to a signal from the controller, transferring the fluid from the mixing assembly to a flow through detector to perform a concentration measurement on the fluid.

There is also provided a novel groundwater sampling device comprising: a controller; a mixing assembly for receiving a groundwater sample and a predetermined volume of a dilution fluid in response to signals from the controller; a flow through detector in fluid communication with the mixing assembly for determining the concentration of a component of the groundwater sample; and an injection assembly in fluid communication with the mixing assembly and a source of baseline fluid, the injection assembly adapted to selectively provide one of at least two dissimilar predetermined volumes of the groundwater sample to the mixing assembly in response to signals received from the controller, the injection assembly including a multiport injection value and at least two sample loops of dissimilar volume in fluid communication with the multiport injection valve, wherein at least two distinct dilutions of the groundwater sample can be automatically provided to the flow through detector for concentration measurements.

There is also provided an automated fluid analysis system comprising: a controller; a mixing assembly for receiving a fluid sample and a predetermined volume of a dilution fluid to form first and second diluted fluid sample, the mixing assembly adapted to form the diluted fluid samples and provide them to a detector for analysis in response to signals from the controller; and an injection assembly in fluid communication with the mixing assembly and a source of dilution fluid, the injection assembly adapted to selectively provide one of at least two dissimilar predetermined volumes of the fluid sample to the mixing assembly in response to signals received from the controller, the injection assembly including a multiport injection value and at least two sample loops of dissimilar volume in fluid communication with the multiport injection valve, the mixing assembly including a multi port selector valve coupled to a syringe pump, the multi port selector valve operable to place the syringe pump in fluid communication with the injection assembly, a second syringe member, and the detector in response to signals from the controller, wherein at least first and second diluted fluid samples can be automatically provided to the detector for analysis in response to signals from the controller.

BRIEF DESCRIPTION OF THE DRAWINGS

Preferred embodiments of the invention are described below with reference to the following accompanying drawings.

DETAILED DESCRIPTION OF SELECTED EMBODIMENTS

Figure 1:
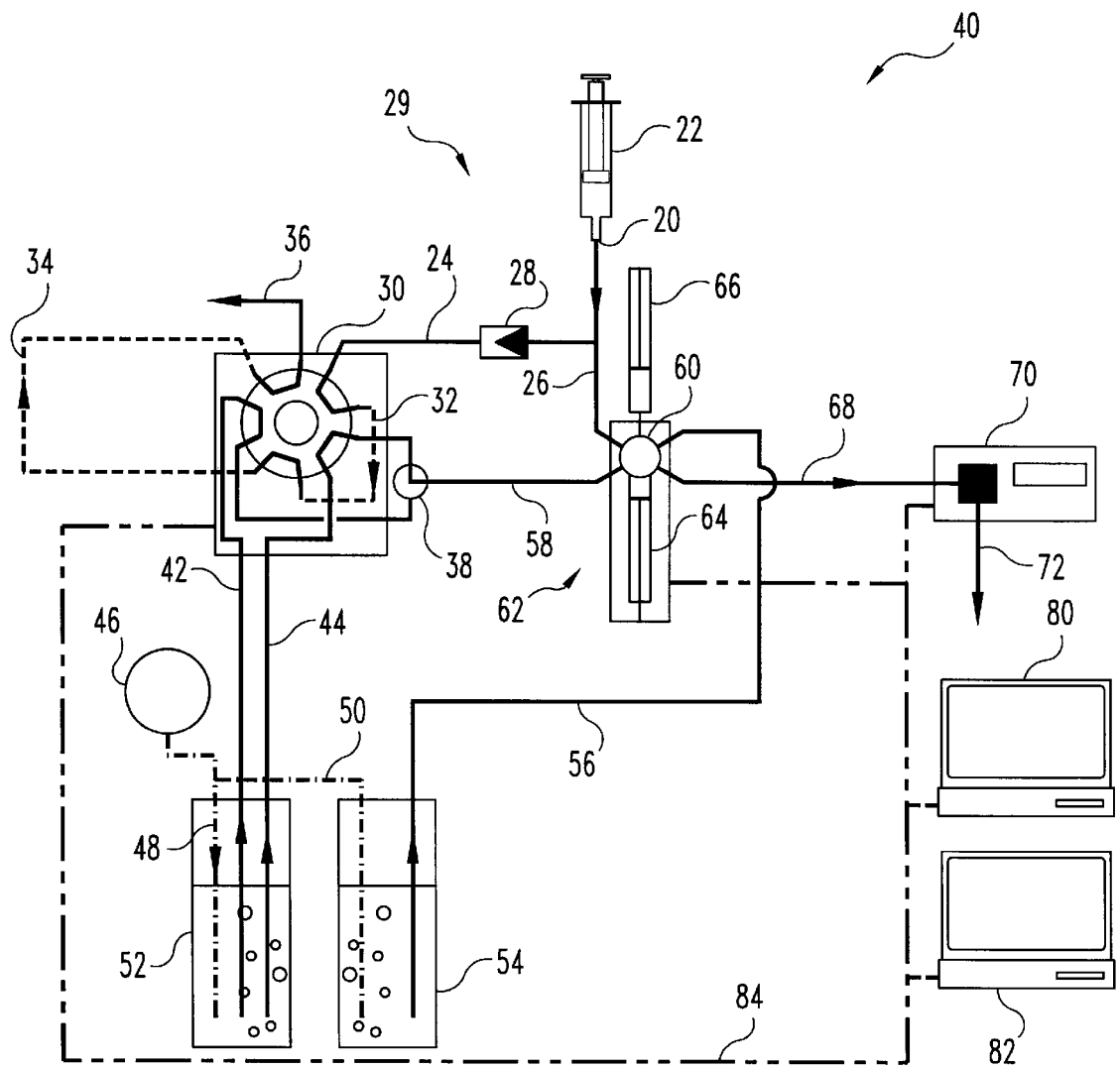
FIG. 1 is a schematic of device for fluid analysis in the sample fill position.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Turning now to FIG. 1 a fluid analysis device 40 is disclosed. Device 40 includes an injection assembly 29 that is adapted to receive a fluid sample and to provide measured volumes of the fluid to a mixing assembly 62. The mixing assembly 62 in turn is adapted to dilute the sample with fluid from fluid chamber 52 and deliver the diluted sample to a detector 70 for analysis.

Injection assembly 29 includes a sample inject port 20 for coupling to a fluid sample. The fluid sample is contained in a sample container 22 such as a sample syringe, though optionally assembly 29 can be configured to draw the sample from a continuous supply of fluid sample such a process line. Injection assembly 29 is adapted to selectively provide predetermined volumes of the sample from container 22 to mixing assembly 62 by at least one of several fluid paths. One fluid path includes branch 26 leading directly to assembly 62. A separate fluid branch reaches assembly 62 through branch 58, via branch 24 and the multi port injection valve 30.

Figure 2:
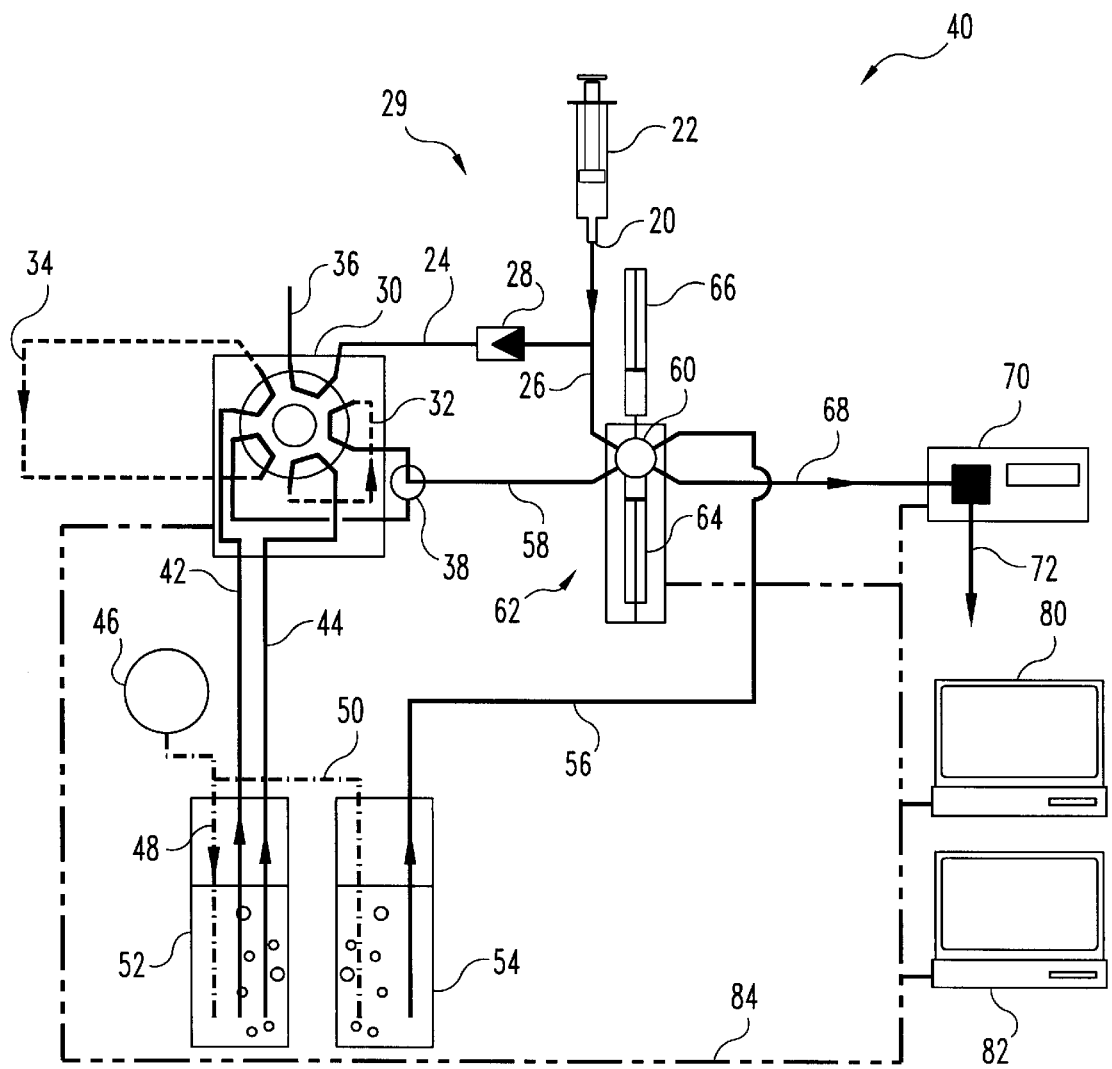
FIG. 2 is a schematic of the device of FIG. 1 in the deliver position.

Referring now to FIGS. 1 and 2, valve 30 is configured to provide two distinct measured volumes of the sample to mixing chamber 62. Valve 30 is a ten port valve coupled to two sample loops 32 and 34 that, when oriented in the "fill" position of FIG. 1, are in fluid communication with each other and the fluid sample at 20. Fluid injected at 20 passes through one way valve 28 and sample loops 32 and 34 and out to waste 36. When valve 30 is turned to the "deliver" position of FIG. 2, loops 34 and 32 contain portions of the fluid sample and are made to communicate with line 58 through three way valve 38. The fluid portions are of dissimilar size, and valve 38 is configured to allow either the small volume of sample in loop 32 or the relatively larger sample in loop 34 to be delivered to assembly 62.

In addition to the sample from sample loops 32 and 34, dilution fluid from container 52 is also provided to mixing chamber 62 through fluid branch 58. When valve 30 is in the "deliver" position of FIG. 2, sample loops 32 and 34 are in fluid communication with fluid lines 44 and 42 respectively. Thusly configured, dilution fluid from chamber 52 can travel through lines 44 and 42, through sample loops 32 and 34, through valve 38, and into mixing assembly 62 via path 58. Alternatively dilution fluid can be provided to apparatus 62 when the injection valve is in the "fill" position of FIG. 1. In this alternative pathway, dilution fluid does not pass through sample loops 32 or 34.

Mixing assembly 62 includes a multiport selector valve 60 coupled to a syringe pump 64, such as one obtainable from Kloehn Co., Las Vegas Nev. Selector valve 60 operates to selectively place pump 64 into fluid communication with any one of the various fluid lines or with a second syringe 66. With the system sealed against air leaks, movement of the plunger in pump 64 causes negative or positive pressure along the fluid path created by selector valve 60. For example, with syringe pump 64 selected to be in communication with branch 26, syringe can be activated to draw fluid from container 22. It is understood that in this situation, one way valve 28 prevents fluid from coming from other parts of the injection assembly 29. Alternatively a three way valve coupling branches 24 and 26 with port 20 could assure sample integrity as well.

With selector valve selecting branch 58 and valve 30 in the deliver position of FIG. 2, operation of syringe pump 64 draws fluid from the selected sample loop (34 or 32) and also from the dilution fluid chamber 52. As described above, the sample loops contain sample, whereas chamber 52 contains dilution fluid. Syringe pump 64 is configured to provide accurate measurement and/or control of the volume of fluid moved in and out of the pump 64. Based on the total volume of fluids drawn into pump 64, the degree of sample dilution can be determined because the volume of sample contained in the selected sample loop is known.

As the dilution fluid and the sample are drawn into syringe 64, some degree of mixing occurs. With syringe 64 filled with a combination of sample and dilution fluid, additional mixing can also be performed. To perform this additional mixing, selector valve 60 is rotated to select the second syringe 66 and the fluid is passed back and forth between syringes 64 and 66 a number of times. The flow patterns and fluid agitation resulting from this action serves to further mix the fluid.

When the fluid is adequately homogenized and contained in syringe 64, selector valve can select line 68 to perform a fluid analysis operation. Syringe pump 64 passes the fluid into a detector. In the illustrated embodiment, detector 70 is a flow through detector 70 and fluid continues out to waste 72. Detector 70 can measure any desired fluid property, and in one embodiment detector measures the concentration of a fluid constituent.

To more accurately determine the concentration, a baseline measurement can also be performed. The baseline data is obtained by filling syringe 64 with fluid from either container 52 or container 54. After running any necessary wash cycles to remove any residual sample from the system, fluid from container 52 or 54 is provided to detector 70 and a baseline measurement is taken. Subtracting the baseline data from the sample data, the concentration of the fluid sample provided to detector 70 can be determined. When the sample has been diluted, for example in mixing chamber 62, the dilution factor is applied to provide the undiluted sample concentration of the detected fluid constituent.

In one application, device 40 is configured to measure the concentration of selected components in groundwater samples. The selected component can be a naturally occurring component, a contaminate, or a remedial chemical applied to treat a contaminate. In one aspect the selected component is dithionite. When testing for dithionite, detector 70 can measure the UV adsorption spectrum of the groundwater sample flowing through detector 70, focusing in particular on UV adsorption at a selected wavelength, namely 315 nm.

The choice of a baseline fluid depends on the characteristics of the sample provided to the detector 70. In one aspect, chamber 52 contains deionized water and chamber 54 contains groundwater (taken prior to any soil modification, such as a dithionite injection). Chambers 52 and 54 are both continuously bubbled with gas, such as helium gas, from gas supply 46 via supply lines 48 and 50 to make the groundwater or deionized water substantially free of oxygen. The degassed deioinized water from chamber 52 is used to dilute groundwater samples contained in sample loops 32 and 34. This dilution can be by a factor of, for example, between 100 and 700. When such a diluted sample is passed into the detector 70, the majority of the fluid is the degassed deionized water from chamber 52. Accordingly, it is appropriate to use chamber 52 as the source of baseline fluid.

By contrast, when an undiluted or substantially undiluted sample is run, the sample is mostly groundwater. To account for the slight matrix effects or trace chemicals of the groundwater, chamber 54 can serve as the source of baseline fluid.

In one application, device 40 is portable and automated, allowing for rapid field analysis of groundwater samples. Device 40 includes controllers 80 and 82 that are connected by signal lines 84 to detector 70, injection assembly 29, and mixing assembly 62. Controllers 80 and 82 control the operation of and record the measurements of detector 70. Controllers 80 and 82 also control the fluid flow operations by controlling valves 30, 38, and 60 and by controlling syringe pump 64. Device 40 further includes a power supply (not shown) such as a battery. Also, while separate controllers 80 and 82 are illustrated, all the control operations can be consolidated into a single controller, such as a computer or workstation.

Figure 3:
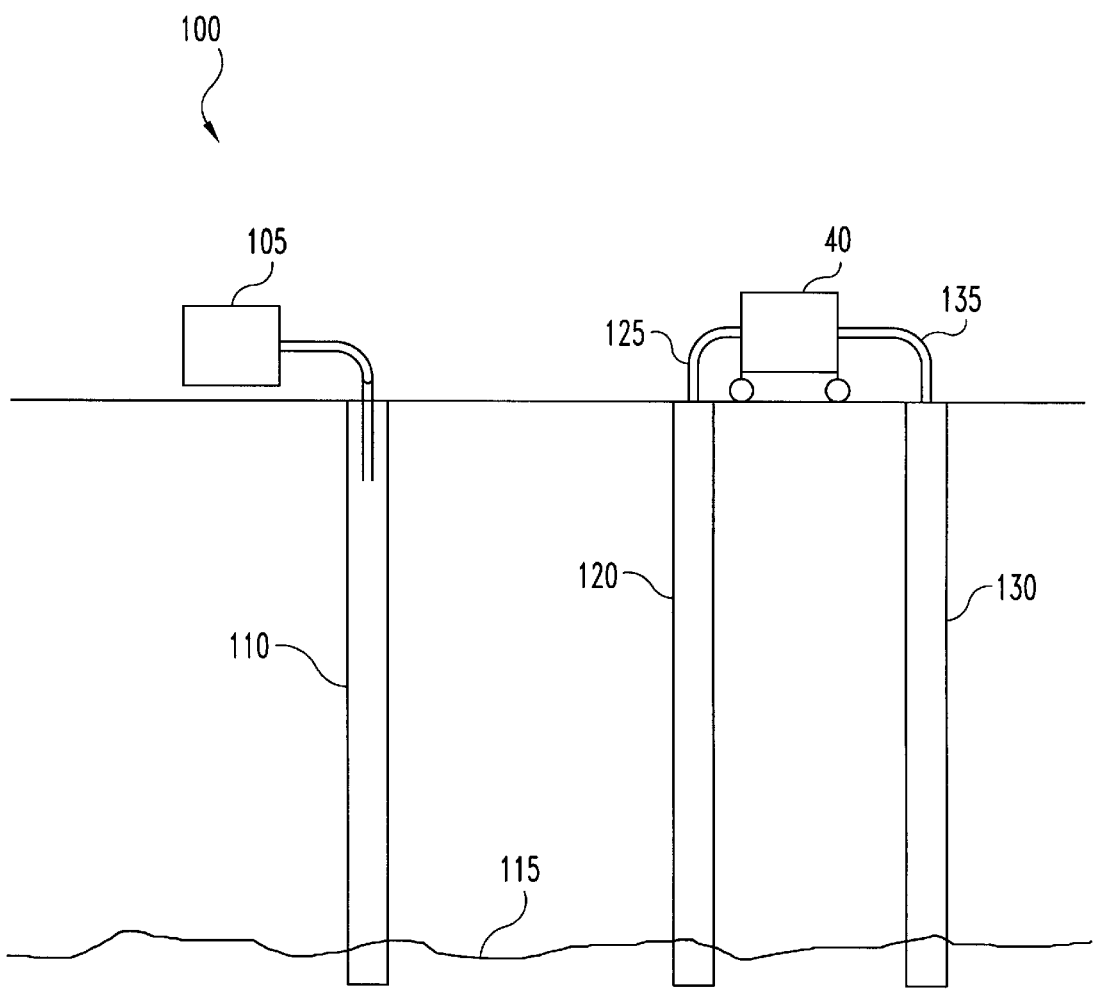
FIG. 3 is a schematic of a field system for monitoring groundwater constituents.

Turning now to FIG. 3, soil treatment and monitoring system 100 is illustrated. In the conventional fashion, a dithionite source 105 delivers dithionite to well 110 in contact with the ground. The dithionite reacts with soil constituents and also enters groundwater 115. At spaced locations from well 110, groundwater 115 is removed from wells 120 and 130 and provided to device 40 through sample conduits 125 and 135. The level of dithionite in the groundwater removed from wells 120 and 130 is monitored as a function of time providing data regarding the effectiveness and extent of the remediation process.

In a typically injection for soil remediation, a highly concentrated dithionite solution, for example between 0.1–0.01 mol/L sodium dithionite, is injected into well 105. Initially, the dithionite concentration at wells 120 and 130 will be negligible. At some point in time after the injection, samples taken from the closer well, well 120 will begin to show effects of the initial injection and the level of dithionite will rise. Later the level of dithionite from the farther well, well 130 will also rise. In each well the dithionite concentration could rise to a level about as high as the concentration of the initial injection after which it can be expected to decline as the dithionite reacts will soil constituents. In most cases the level will decline to approximately zero as all the dithionite will react with soil constituents.

Figure 4:
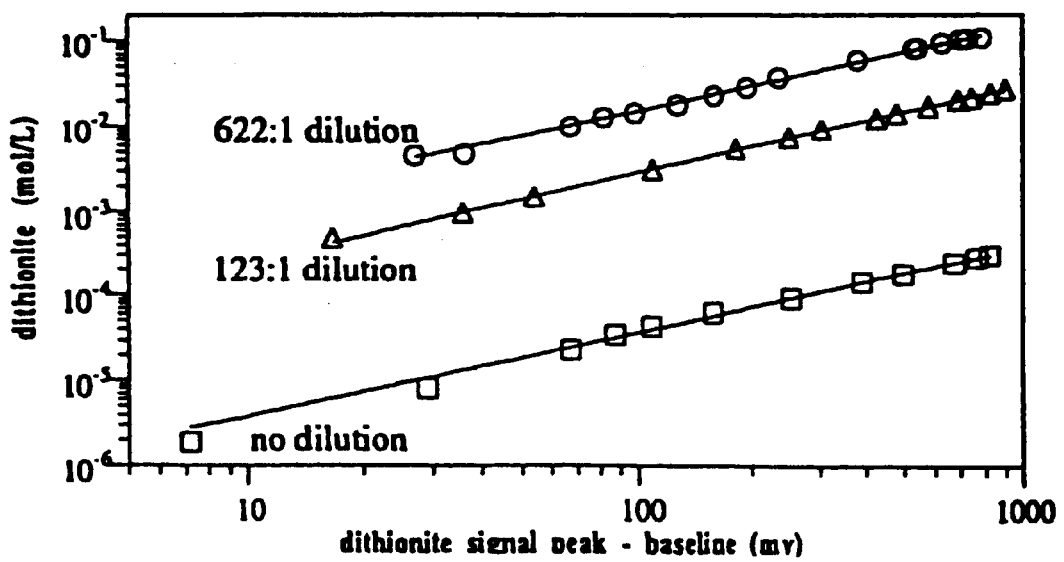
FIG. 4 is a graph of dithionite concentration versus the dithionite signal peak above the baseline signal at three different dilution levels.

As can be appreciated, the concentration of dithionite in solution at any one monitoring well 120, 130 can be expected to range from zero to 0.1 mol/L. However, most UV adsorption apparatus can only accurately detect concentrations of dithionite less than about 0.0002 mol/L dithionite, though the limits and range will vary with the specific instrument used. Accordingly, more concentrated samples must be diluted to obtain a useful absorbance signal. A typical UV absorbance signal versus the pre-diluted dithionite concentration is shown in FIG. 4 for three typical dilution levels.

Based on the expected pattern of dithionite concentrations, the system 100 can be configured to optimize the sampling routine to minimize the number of wasted runs (where the sample concentration is outside the detector range) yet able to accurately obtain dithionite concentrations throughout the entire process. Controllers 80 and 82 can include a clock and data processor that identifies any given sample as coming from a particular well (known distance from the injection well) at an identified time after the start of the remedial injection. Alternatively or in addition, this information can be manually entered by an operator.

To begin, an adequate supply of a groundwater sample is delivered to port 20. A portion of the groundwater is injected or otherwise delivered to fill sample loops 32 and 34, assuring that the pure groundwater has displaced any fluid in the loops out to waste. The remainder of the sample remains in container 22 attached at port 20.

The first sample from a monitoring well (120, 130) after injection can be expected to be of low dithionite concentration. Thus controller 80 or 82 sends a signal to cause the sample at be evaluated at no dilution by directly drawing the sample still contained at 22 into syringe pump 64 through conduit 26. The sample is then fed to detector 70. If the absorbance signal is above a threshold amount, for example 1000 mV, then the measured concentration is deemed inaccurate and the controller signals a start of a second run.

The second run can be a more diluted run obtained by drawing the sample from large loop 34 and a quantity of fluid from 52 into syringe 64. After appropriate mixing, the now diluted sample is fed to detector 70. If this dilution level also yields a signal above the threshold amount, this concentration measurement is deemed inaccurate and a third measurement is taken.

The third measurement can be at a higher level of dilution and occurs by pulling sample from loop 32 and dilution fluid from 52 into syringe 64. After appropriate mixing, the diluted sample is fed to detector 70 and the measurement is recorded.

It is understood that if any of the earlier measurements yields a reading within the machine confidence range, the concentration is calculated from that measured value and no further diluted or undiluted samples need be run. Likewise, when the concentration is expected to be declining a lower signal threshold can trigger running a less diluted sample.

In addition, successive runs of the groundwater samples taken from a particular well can start the process at either the no dilution level, the medium dilution level, or the high dilution level based on the results of the previous samples from that well. The dilution level can be selected based on the expected concentration of dithionite calculated by extrapolation from prior data, and the dilution level adjusted, either up or down, based on a high and low signal threshold for the flow through detector.

In addition to adjustments to the dilution level of a particular sample, the sampling interval can also be automatically adjusted based on data obtained from the detector. For example, based on the relative concentration change between previous samples, the time interval before taking the next sample can be adjusted to capture additional data points when the concentration is more rapidly changing.

To assure sample integrity, the system is flushed prior to or after running each sample. For example after running a sample from one of sample loops 32 and 34, syringe 64 draws a volume of fluid from container 52 through the sample loop and flushes it out through the detector (where no signal is taken) after being passed back and forth between syringes 66 and 64. Several other volumes of fluid are likewise flushed prior to the controller signaling the detector to beginning taking the baseline measurement. This procedure is followed for each of the samples in loops 34 and 32.

Where the sample is drawn from conduit 26, an initial portion of the sample is drawn into syringe 64 and discarded through the detector 70 to flush out any residual fluid from previous runs remaining in conduit 26. The volume needed to adequately flush the system depends on the volume of conduit 26, which can be minimized by locating port 20 on close proximity to valve 60. Then the desired sample volume is drawn into syringe 64 to be analyzed by detector 70. Next, prior to taking the baseline measurement, several volumes of fluid from container 54 are flushed to clean out syringe 64.

For each of the UV readings, including the sample concentration readings and the baseline readings, the time average of the UV absorbance is taken. With syringe 64 containing a know volume and moving at a constant rate, the sample fluid flow time through the detector 70 can be calculated. It has been found that more accurate results are obtained by averaging the middle portion of the sample stream and discarding the signal from the beginning and end of the sample flow.

In is also advantageous to control the speed of fluid travel, by controlling the speed of syringe pump 64, to avoid cavitation, for example when moving fluid through small inner diameter portions of the assembly such as sample loops 34 and 32. In addition, a filter can be placed at the injection port 20 to filter out sediments from entering and clogging the machine.

In is also understood that each of the dilution levels can be selected and controlled based on the volume of the sample relative to the volume of the dilution fluid drawn into syringe pump 64. The range of dilution are selected to bring the range of expected concentrations into the concentration range directly measurable by the detector. The total volume of fluid drawn into syringe pump 64 can be roughly equal for each dilution, the relative volumes of the sample loops varying by a factor of at least 2 and more preferably between 2 and 10. In other variations the total volume of fluid drawn into syringe 64 is substantially greater when a higher dilution level is desired.

In other aspects of the invention, detector 70 can be any detector that is sensitive and accurate over a limited range. Non limiting examples include HPLC detectors such as UV absorbance, florescence, pulsed electrochemical detectors, refractive index detectors, specific ion electrodes, and mass spectrometers. Where the device is used on a gas stream, typical gas detectors such as electron capture detectors, flame ionization detectors, thermal conductivity detectors, and mass spectrometers can be used. In addition, intermediate fluid analysis procedures can be performed manually or automatically with the diluted fluid samples exiting apparatus 62 prior to analysis in detector 70.

It is to be understood that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

EXHIBIT A
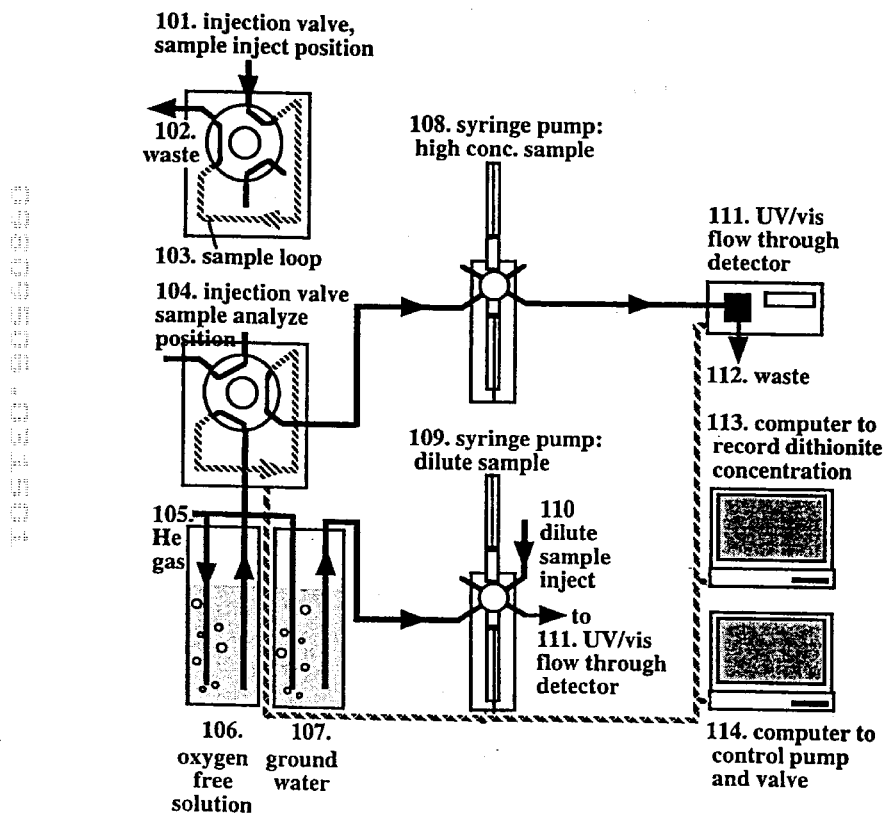

EXHIBIT B

Dithionite System Setup and Operation

Pacific Northwest National Laboratories
Jim Szecsody

Overview

The dithionite system is used to measure the concentration of sodium dithionite, which is the reactant that will reduce iron in sediment. As sodium dithionite reacts, other sulphur products are produced (thiosulfate, sulfite, sulfate), which do not react with sediment (and are not measured with the dithionite system. The system dilutes a sample with deionized, degassed water so that the dithionite concentration can be measured by ultraviolet light (UV) absorbance in a range of most detectors.

The basic components of the dithionite system are: a) injection valve (where sample is injected), b) syringe pump (with 2 glass syringes on it), c) computer controlling syringe pump, d) UV detector, e) data logging computer. When a sample is injected at the injection valve, sample liquid flows through a low volume steel loop (typically 15 to 100 microliters) and out to a waste container. A minimum of 2 mL should be injected to be sure the sample has been injected past the filter (hold volume about 0.6 mL). When the syringe pump program is initiated, this sample is pulled into one of the glass syringes with ~10 milliliters of degassed water, mixed, then injected to the UV detector. After the sample is injected, two separate cycles of degassed water (no sample) are flushed through the system to stop sample carryover from sample to sample. The dithionite concentration is recorded as the difference in peak millivolt signal between the sample and a second solution of just the degassed water (second cycle of degassed water). The peak and baseline UV signal is manually recorded as well as automatically logged by a computer (peak concentration only). A separate spreadsheet is used to calculate the dithionite concentration from the two UV values.

Physical Setup of Dithionite System 1. fill the deionized water bottle, empty waste bottle, and place the frame containing these bottles as well as valves and syringe pumps in a suitable location.

2. Approximately 11 amps of 120v fairly clean power is needed. Large cycling pumps or other high load devices can affect the operation of the computers and detector. All devices of the dithionite system are hooked up to two power strips, so these are plugged into external power. Cycling of the ground water pumps specifically caused problems, so the dithionite system should be on a different breaker.

3. Place the UV detectors (Linear UVIS 200, Isco V4) on the left top of the framework, and the portable computer on the right top of the framework. Plug the UV detector output signal (BNC plug) into the data logging board. Plug syringe pump #1 serial connector into the portable computer. Attach the input and output tubing of the detector to the labeled fittings. Attach helium gas to the flow meter on the deionized water bottle. Helium is used to sparge (bubble through) the water to displace oxygen and other gasses. Helium solubility is orders of magnitude lower than other gasses, so this effectively degasses the water. Low flow rates (100 - 300 mL/min) of gas flow are needed, so a 2-stage regulator should be used on the helium tank. Ultra pure helium should be used (trace oxygen has been removed).

Startup 1. turn on the helium gas supply and adjust the flow to 300 mL/minute (rapid bubbling should be observed). This should continue for 30 minutes, then the gas flow rate can be decreased to 100 mL/min and the following steps be initiated.

2. turn on both power strips, computers, and the UV detector. The UV detector lamp has a limited life (750-1000 h), so should not be left on for days if not needed. It also takes 1-2 h to stabilize after being turned on. There should be a value displayed in the "absorbance" window (any number) when the lamp is lit. On the portable (syringe pump) computer, type "win" to start windows.

3. starting/initiating the syringe pump and program. The red toggle switched at the upper center of the framework should be switched on. On the syringe pump with windows operating, double click on the "winpump" icon. Press the "OK" button for "COM1" being the default commumication. Under "file", load the program "di10ml.gpl" (a list of commands will appear on the right half of the screen). Most of the setup commands should be correctly loaded from the program, but this should be checked. With WinPump running, go through all of the setup commands under the "Options" pulldown:
a) host communication = com1 at 9600, DT protocol
b) pump selection = 1
c) syringe type = 10,000 microliter
d) host valve setting = 6-way valve, distribution
e) model selection = 48,000 step model
f) expansion port = 2-byte serial mode Under the "commands" menu, execute "initialize syringe". With the left mouse button, click on the "go to soft stop" button (W valve port = A should also be selected), then click on the "go" button. MANUALLY move the thumbwheel at the bottom of the syringe pump to move the location of the plunger of the lower glass syringe to 0.0 mL. This is a location right before there started to be a lot of resistance on the thumbwheel. Now click on the "set home" button, then click on "go" and the syringe pump should cycle back to this 0.0 mL position. If there are error commands, go though the setup commands and try restarting the syringe pump (i.e., turn power off/on).

4. test syringe pump program. Under the "program" menu, execute "run listed program". The highlighted step should stop at the third line (line 2 = "halt"). Execute "run listed program" again and the entire program should be executed and it should restart at the top and end on line 3. If there are any error commands, under "program", execute the "terminate" command (stops the program), then go through the steps listed under item #3. The program should be cycled 2-3 times before a sample is analyzed. This will fill the syringe, tubing, and valves with degassed water. Press the "zero" button on the UV detector.

5. test the dithionite system operation. Inject a standard concentration of dithionite 3-5 times (steps described under "measuring dithionite"). The peak signal (i.e., dithionite concentration) will increase with each injection and level off after 3-4 runs. If the dithionite concentration continues to increase, the water is not degassed, so increase the helium flow and wait 30 minutes.

Measuring Dithionite Concentration

1. inject sample
These steps assume the startup of the system was successful. Inject 2 to 5 milliliters into the loop at the valve through a 25-mm diameter (0.45 μm pore diameter) filter. There should be some resistance to injecting the sample (it should take 10-15 seconds to inject a few milliliters). If there is too much resistance, change the filter. The filter should last 10-20 injections.

2. start program
At the syringe pump computer, the highlighted step should be #7 (acceleration rate = 4). Under the "program" menu, execute "run listed program". If the program was not at step #7, under the "program" menu, execute "terminate" and click the left mouse button at step 7, then execute the "run listed program" command. The program takes about 6 minutes to complete.

3. record concentration
Recording the peak absorbance. Follow the lines of the program as they are executed. Executing step 28 (absolute position = 1000 microliters) will take about 2 minutes. During this time interval, record the maximum absorbance value (in millivolts) on the screen of the data logging computer. This will generally be from looking at the "MT1, uv#1 peak" window (which lists the maximum value within the last two minutes). Write down this value under "Sample, 315 nm" on the data sheet. In general, the dithionite concentration will look like a square wave on the graph (data logging computer). If there are large swings in the value over the 2 minute interval, rerun the sample.

4. record background (baseline) concentration
Recording the baseline absorbance. Two cycles of degassed water will be passed through the system in steps 35 through 47. In the last cycle, when executing step 47 (step 48 is highlighted when step 47 is being executed), record the maximum value of absorbance observed from the "MT5 UV#1" window (and NOT the MT1 UV#1 peak window). Step 47 will take about 20 seconds to complete. The values jump around a few tens of millivolts. Write down the baseline value on the data sheet.

5. calculate dithionite concentration
At the computer where the dithionite spreadsheet is open, enter the peak and baseline values and the dithionite concentration (in moles/liter) are calculated.

6. limitations of measuring dithionite concentration
There are limitations to what dithionite concentrations can be measured with a specific setup. Using a specific loop and total volume, about two orders of magnitude of dithionite concentration can be measured. With a combination of 3 different loops and different programs, about 6 orders of magnitude of concentration can be measured. Since two systems are built, it might be efficient to have one system set up for low concentration and one for high concentration.

In general, there is a linear relationship between the millivolt response (absorbance) and concentration if the absorbance is below 1.0 absorbance units (1000 millivolts). Therefore, very high concentrations will have to be manually diluted externally before injecting into the system. If a sample absorbance is >>1000 millivolts (1 absorbance unit or AU), then it should be reinjected after manual dilution. Manual dilution is accomplished by using water from the syringe luer fitting to the right of the syringe pump #2. For example, 9 mL of degassed water mixed with 1.0 mL of sample water gives a total dilution factor of 10.0. This dilution factor is entered on the data sheet and excel spreadsheet (incorporated into the calculation).

Periodic Adjustments and Maintenance 1. syringe pump. The upper glass syringe should contain no water when the system is not running. It can slowly fill up with water over many injections and should be emptied when there is any observable fluid. Partially unscrew the syringe and press the plunger (water will drip over the syringe pump head), and tighten the syringe back in. All of these fittings on the syringe pump head are not overly tight.

2. Degassed water reservoir. When the level is down by 1/3 or more, refill with deionized water. Note that it will then take 30-45 minutes before the water is degassed (so no samples can be run).

3. Effluent waste reservoir (behind the degassed water bottle). Empty when full by holding the lid in one place (with tubing attached) and rotating the bottle.

4. detector. The detector should be rezeroed periodically, if baseline drift is observed. Drift can be caused by electronic warmup of the lamp and/or precipitates building up in the flow through cell. After the dithionite injection is completed (or excessive baseline drift is observed) the detector cell should be cleaned by injecting a mixture of EDTA chelate and acid ("radicawash") or dilute hydrochloric acid (1.0 M) for a few minutes, then deionized water. This injection should be made by manually hooking up a syringe to the inlet tubing of the detector.

5. partial shutdown. If the dithionite system is not going to be used overnight, leave everything on. If the dithionite system is not going to be used for a few days, a complete shutdown is not necessary, but turning off the UV lamps will save considerable cost (they have a limited life). For this partial shutdown mode, turn off the UV detectors and leave everything else on. The Linear lamp has a mean lamp lifetime of 500 hours; the Isco lamp has a mean lamp lifetime of 9000 hours. Both lamps cost ~$500.

6. complete shutdown. Deionized water should be injected into the sample location and a cycle run to flush out any remaining high concentration sample that could cause precipitate. Remove and dispose of used filters. Quit the syringe pump programs and turn off computers. Turn off UV detectors.

Equipment Replacement 1. plastic, stainless steel tubing, 1/16" and 1/8" fittings: Upchurch Scientific, 619 West Oak Street, Oak Harbor, WA 98277, 800-426-0191

2. Isco UV detector: Isco, Inc. 4700 Superior Street, Lincoln, NE 68505, 800-228-4250
Linear UV detector: Alltech, 2051 Waukegan Road, Deerfield Il 60015, 800-255-8324

3. Injection valves (stainless steel): Valco/VICI PO Box 55603, Houston, Tx 77255-5603, 713-688-9345

4. syringe pumps: Kloehn Co., Inc., 10,000 Banburry Cross Dr., Las Vegas, NV 89134, 800-358-4342

5. data logging board on PCI slot, capable of serial control of syringe pumps: National Instruments DAQCARD-500. National Instruments, 6504 Bridge Point Parkway, Austin, Tx 78730, 512-683-0100.

I claim:

1. A method for monitoring levels of soil chemicals following a remediation injection, comprising:

providing a groundwater sample to an apparatus comprising a sample injection assembly operatively coupled to a controller, the injection assembly adapted to selectively provide one of at least two predetermined volumes of a fluid sample to a mixing assembly in response to signals received from the controller, the injection assembly including a multiport injection value and at least two sample loops, selecting one of the at least two predetermined volumes of the fluid sample, transferring the selected volume of the fluid sample to the mixing assembly in response to a signal from the controller, transferring a predetermined volume of dilution fluid to the mixing assembly, mixing the predetermined volumes of dilution fluid and fluid sample to create a first diluted fluid sample, performing a concentration measurement on the first diluted sample.

2. The method of claim 1 further comprising:

selecting a second one of the at least two predetermined volumes of the fluid sample, transferring the second selected volume of the fluid sample to the mixing assembly, the second selected volume being dissimilar to the first selected volume, transferring a second predetermined volume of dilution fluid to the mixing assembly, mixing the second predetermined volumes of dilution fluid and the second selected volume of fluid sample to create a second diluted fluid sample, performing a concentration measurement on the second diluted sample.

3. The method of claim 1 comprising calculating the level of dithionite in the groundwater sample.

4. The method of claim 1 wherein the injection assembly includes a sample inlet port able to be placed in fluid communication with the multiport injection valve and the mixing assembly such that fluid can be delivered from the sample inlet port to the mixing assembly without passing through the multiport injection valve.

5. The method of claim 4 wherein the multiport injection valve has at least 10 ports, and wherein the injection assembly includes a three way valve in fluid communication with the sample loops and the mixing assembly.

6. The method of claim 5 wherein the dilution fluid is substantially oxygen-free water, and wherein the sample loops are of dissimilar volume.

7. The method of claim 3 wherein the concentration measurement is performed by a flow through detector in fluid communication with the mixing assembly.

8. The method of claim 1 wherein the mixing assembly includes a multi port selector valve coupled to a syringe pump, the multi port selector valve operable to place the syringe pump in fluid communication with the injection assembly, a second syringe member, and a flow through detector in response to signals from the controller.

9. The method of claim 8 further comprising:

transferring a volume of dilution fluid to the syringe pump, performing a baseline measurement on the dilution fluid.

10. The method of claim 9 wherein the dilution fluid is oxygen free water.

11. A method for monitoring levels of soil chemicals following a remediation injection, comprising:

providing a groundwater sample to an apparatus comprising a sample injection assembly operatively coupled to a controller, the injection assembly adapted to automatically provide one of at least two dissimilar predetermined volumes of a fluidsample to a mixing assembly in response to signals received from the controller, the injection assembly including a multiport valve in fluid communication with at least one sample loop, the injection assembly further including a sample inlet port able to be placed in fluid communication with the multiport valve and the mixing chamber, selecting one of the at least two dissimilar predetermined volumes of the fluid sample, transferring the selected volume of the fluid sample to the mixing assembly in response to a signal from the controller, transferring the fluid from the mixing assembly to a flow through detector to perform a measurement of the concentration of soil chemicals on the fluid.

12. The method of claim 11 further comprising:

transferring a volume of dilution fluid to the flow through detector through the mixing assembly to provide a baseline value for determining concentration from the concentration measurement.

13. The method of claim 12 wherein:

the dilution fluid is oxygen free water and the concentration of dithionite in groundwater is determined.

14. The method of claim 10 further comprising:

selecting a second one of the at least two dissimilar predetermined volumes of the fluid sample, transferring the second selected volume of the fluid sample to the mixing assembly.

15. The method of claim 14 wherein:

the multiport valve is in fluid communication with at least two sample loops of predetermine volume and the second predetermined volume of fluid sample is selected based on information obtained from the flow through detector.

16. The method of claim 10 wherein:

the mixing assembly includes a multi port selector valve coupled to a syringe pump, the multi port selector valve operable to place the syringe pump in fluid communication with the multiport injection valve, the sample inlet port, a second syringe member, and the flow through detector in response to signals from the controller 17. A groundwater sampling device comprising:

a controller;

a mixing assembly for receiving a groundwater sample and a predetermined volume of a dilution fluid in response to signals from the controller;

a flow through detector in fluid communication with the mixing assembly for determining the concentration of a component of the groundwater sample; and an injection assembly in fluid communication with the mixing assembly and a source of baseline fluid, the injection assembly adapted to selectively provide one of at least two dissimilar predetermined volumes of the groundwater sample to the mixing assembly in response to signals received from the controller, the injection assembly including a multiport injection value and at least two sample loops of dissimilar volume in fluid communication with the multiport injection valve, wherein at least two distinct dilutions of the groundwater sample can be automatically provided to the flow through detector for concentration measurements.

* * * * *

UNITED STATES PATENT AND TRADEMARK OFFICE
CERTIFICATE OF CORRECTION

PATENT NO. : 6,706,527 B2  
DATED : March 16, 2004  
INVENTOR(S) : James E. Szecsody It is certified that error appears in the above-identified patent and that said Letters Patent is hereby corrected as shown below:

Columns 9-22 are deleted.

Signed and Sealed this

Eighteenth Day of May, 2004

JON W. DUDAS  
*Acting Director of the United States Patent and Trademark Office*